(12) United States Patent
Inacio et al.

(10) Patent No.: US 11,844,860 B2
(45) Date of Patent: Dec. 19, 2023

(54) PHARMACEUTICAL FORMULATION FOR INTRADUODENAL ADMINISTRATION COMPRISING MELEVODOPA AND CARBIDOPA

(71) Applicant: CHIESI FARMACEUTICI S.p.A., Parma (IT)

(72) Inventors: Ricardo Inacio, Parma (IT); Mark Saunders, Parma (IT); Bhanvi Mehta, Parma (IT); Kathrin Muehlhoelzl-Odoerfer, Parma (IT); Isabel Sole Font, Parma (IT); Grazia Caivano, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 505 days.

(21) Appl. No.: 16/977,232

(22) PCT Filed: Feb. 21, 2019

(86) PCT No.: PCT/EP2019/054329
§ 371 (c)(1),
(2) Date: Sep. 1, 2020

(87) PCT Pub. No.: WO2019/166322
PCT Pub. Date: Sep. 6, 2019

(65) Prior Publication Data
US 2021/0007984 A1    Jan. 14, 2021

(30) Foreign Application Priority Data
Mar. 2, 2018 (EP) .................... 18159758

(51) Int. Cl.
| | |
|---|---|
| *A61K 9/08* | (2006.01) |
| *A61K 9/00* | (2006.01) |
| *A61K 9/51* | (2006.01) |
| *A61K 31/198* | (2006.01) |
| *A61K 31/223* | (2006.01) |

(52) U.S. Cl.
CPC ............. *A61K 9/08* (2013.01); *A61K 9/0019* (2013.01); *A61K 9/5123* (2013.01); *A61K 9/5138* (2013.01); *A61K 9/5161* (2013.01); *A61K 9/5192* (2013.01); *A61K 31/198* (2013.01); *A61K 31/223* (2013.01)

(58) Field of Classification Search
CPC ....................................................... A61K 9/08
See application file for complete search history.

(56) References Cited

U.S. PATENT DOCUMENTS

| | | |
|---|---|---|
| 4,826,875 A | 5/1989 | Chiesi |
| 5,017,607 A | 5/1991 | Chiesi |
| 2018/0021280 A1 | 1/2018 | Deac et al. |

FOREIGN PATENT DOCUMENTS

| | | |
|---|---|---|
| EP | 0 252 290 A2 | 1/1988 |
| WO | 2018/017850 A1 * | 1/2018 |
| WO | WO 2018/017850 A1 | 1/2018 |

OTHER PUBLICATIONS

Fox et al, The Movement Disorder Society: Evidence-Based Medicine Review Update: Treatment for the Motor Systems of Parkinson's Disease, Movement Disorders, vol. 26. pp. 1-40. (Year: 2011).*

Fox et al., The Movement Disorder Society: Evidence Based Medicine Review Update: Treatment for the Motor Systems o Parkinson's Disease Movement Disorders, vol. 26, pp. 1-40 (Year: 2011).*

Tamasco et al., Levodopa in Parkinson's Disease Current Status and Future Developments, Current Neuropharmacology, 16, 1239-1252. (Year: 2018).*

International Search Report and Written Opinion dated May 7, 2019 in PCT/EP2019/054329 filed on Feb. 21, 2019.

Extended European Search Report dated Sep. 18, 2018 in European Application 18159758.4 filed on Mar. 2, 2018.

* cited by examiner

*Primary Examiner* — Carlos A Azpuru
(74) *Attorney, Agent, or Firm* — Oblon, McClelland, Maier & Neustadt, L.L.P.

(57) ABSTRACT

A pharmaceutical formulation for intraduodenal administration comprising melevodopa and carbidopa as active ingredients and one or more excipients. Once dispersed in an aqueous medium, melevodopa is completely dissolved, and carbidopa is present as nanoparticles.

16 Claims, No Drawings

PHARMACEUTICAL FORMULATION FOR INTRADUODENAL ADMINISTRATION COMPRISING MELEVODOPA AND CARBIDOPA

CROSS REFERENCE TO RELATED APPLICATIONS

This application is a 371 of International Patent Application No. PCT/EP2019/054329, filed on Feb. 21, 2019, and claims priority to European Patent Application No. 18159758.4, filed on Mar. 2, 2018, both of which are incorporated herein by reference in their entireties.

TECHNICAL FIELD

The present invention relates to a pharmaceutical formulation for intraduodenal administration.

More specifically, the invention relates to a formulation for the treatment of severe Parkinson's disease comprising melevodopa and carbidopa.

BACKGROUND OF THE INVENTION

Parkinson's disease is characterized by a progressive degeneration of the dopaminergic nigrostriatal pathways in the brain.

Biochemical studies carried out in the sixties lead to the discovery of the fundamental role played in the pathogenesis of this disease by the deficit of neurotransmitters, and particularly of dopamine.

This important advance in the comprehension of the neurochemical bases of the pathology brought about a drastic change in the pharmacological approach to the disease, and lead to the introduction in the therapy of an immediate biologic precursor of dopamine, (−)-3-(3,4-dihydroxyphenyl)-L-alanine, more commonly known as levodopa or L-DOPA.

Levodopa, in particular in combination with the DOPA carboxylase inhibitor carbidopa, has found a wide use for the treatment of patients suffering from Parkinson's disease, and good results are achieved by said treatment. However, it is important in such a treatment that a stable level of the active agent is maintained in the patient's blood, and this has often been difficult to achieve in more conventional ways of administration.

In fact, the introduction of supplemental levodopa, alone or in combination with carbidopa, is associated with an increase in the frequency of motor complications.

Therefore, it has hence been highlighted that more continuous delivery of levodopa might improve Parkinson's disease therapy and be associated with a reduced risk of motor complications.

In several reports, the use of intraduodenal administration of aqueous solutions of drugs have shown several advantageous features as compared to oral administration of tablets, suspensions and solutions (e.g. Watari et al., J Pharmacokinet Biopharm 1983 11 (5), 529-545; Ruggeri S et al The Lancet, 1989 2, 45-46). Especially, the variation of drug plasma concentration was substantially reduced by using the intraduodenal route, mainly due to avoidance of the effect of variations in gastric emptying times.

On the other hand, it has been difficult to prepare liquid dosage forms, as both the compounds, levodopa and carbidopa, have a very low solubility in water, so that large volumes of liquid have to be administered in order to give the patient an adequate dose. Furthermore, said compounds, being catechol derivatives, are quite sensitive to oxidation, and hence will quickly decompose in aqueous solutions, upon contact with atmospheric air.

These problems have been faced and partially solved in EP 670713, EP 2063865 and WO 2018/017850, disclosing formulations wherein both drugs are in suspended form.

Said formulation is marketed as Duodopa™ and is delivered by a portable pump intraduodenally through an intraduodenal catheter through the abdominal wall of the patient.

However, being a suspension, the formulation could only be administered at a relatively low concentration, i.e. 20 mg levodopa and 5 mg carbidopa per ml, hence requiring high liquid volumes and a catheter with a rather big diameter to avoid clogging. This in turn makes necessary the use of a rather bulky infusion pump such as the CADD-legacy 1400 pump (Smiths Medical, St Paul, USA) affecting patient compliance.

Moreover, suspension formulations may suffer of physical stability problem with risk of sedimentation of drug particles during storage and administration.

In view of the above problems, it would be advantageous to provide a more concentrated formulation for intraduodenal delivery to be administered with a smaller infusion pump, wherein the active ingredients are not in suspended form.

The problem is solved by the present invention which is directed to a powdery pharmaceutical formulation for intraduodenal administration comprising carbidopa and melevodopa as active ingredients, in a ratio of 1:5 by weight, and one or more suitable excipients, wherein upon dispersion in an aqueous vehicle, melevodopa is completely dissolved and carbidopa is present as nanoparticles.

Melevodopa is the methyl ester of (−)-3-(3,4-dihydroxyphenyl)-L-alanine.

Aqueous solution of melevodopa, optionally in combination with carbidopa or benserazide, have first been disclosed in EP 252290.

U.S. Pat. No. 6,284,272 discloses pharmaceutical compositions in the form of effervescent or fast-dissolving tablets comprising combination of melevodopa and carbidopa, as active ingredients.

Stocchi F. et al., Arch Neurol 2005 62, 905-910 reported about the intraduodenal administration of melevodopa.

None of the cited documents has anticipated all the features of the formulation of the present invention.

SUMMARY OF THE INVENTION

In a first embodiment, the present invention is directed to an aqueous pharmaceutical formulation for intraduodenal administration comprising carbidopa and melevodopa as active ingredients in a ratio of 1:5 by weight, and one or more excipients, wherein melevodopa is completely dissolved, and carbidopa is present as nanoparticles having a volume diameter comprised between 100 and 1000 nm, preferably from 200 to 900 nm.

Advantageously, the concentration of melevodopa is comprised between 50 and 150 mg/ml, preferably between 100 and 125 mg/ml expressed as levodopa, and the concentration of carbidopa is comprised between 5 and 30 mg/ml expressed as carbidopa anhydrous, preferably between 10 and 20 mg/ml, more preferably between 15 and 20 mg/ml.

In a particular embodiment, the carbidopa nanoparticles could be prepared by wet bead milling.

In another embodiment, the carbidopa nanoparticles could be prepared by micro jet reactor technology.

By means of the latter technology, at least one among the excipients is adsorbed on the surface of the carbidopa particles in such a way as that the latter ones are coated by the excipient.

In a second aspect, the invention is directed to a process for preparing the claimed formulation comprising the steps of adding the carbidopa nanoparticles to an aqueous solution comprising melevodopa, and one or more excipients.

In an alternative embodiment, the formulation of the invention could be in form of powder to be reconstituted before use, preferably a lyophilized powder.

Therefore, the invention is directed to a process for preparing the claimed formulation in form of lyophilized powder comprising the steps of: i) adding the carbidopa nanoparticles to an aqueous solution comprising melevodopa and at least one or more cryoprotectant agents as excipients; and ii) removing the residual water by drying, for example by spray-drying or freeze-drying, preferably freeze-drying.

In a third aspect, the invention is directed to the claimed formulation for use in the treatment of Parkinson's disease.

In a fourth aspect, the invention is directed to the use of the claimed formulation in the manufacture of a medicament for the treatment of Parkinson's disease.

In a fifth aspect, the invention provides a therapeutical method comprising administering intraduodenally a therapeutically effective amount of the claimed formulation to a patient suffering from Parkinson's disease.

In a sixth aspect, the invention is directed to a kit comprising: a) the claimed pharmaceutical formulation in form of powder to be reconstituted in water before use; b) a pharmaceutically acceptable aqueous vehicle; c) container means for containing the pharmaceutical formulation, and the aqueous vehicle; d) an infusion pump.

Definitions

With reference to melevodopa and carbidopa, the terms "drug", "active ingredient" and "active substance" are used interchangeably.

The term "nanoparticles" means particles having a volume diameter comprised between 1 and 1000 nanometers in size. Said diameter can be determined according to methods known to the skilled person in the art, for example with Dynamic Light scattering (DLS), Transmission Electron Microscopy (TEM) or by the Coulter technique.

The term "anti-solvent" means a liquid having little or no solvation capacity for the drug.

The term "safe" means a pharmaceutical formulation suitable for intestinal infusion able of satisfying the injectability criteria for medicinal products, and well tolerated by the patients.

The expressions "water soluble" and "water insoluble or poorly water soluble" are used with reference to the solubility in water as defined in the European Pharmacopoeia Ed. $4^{th}$, 2003, page 2891.

The expression "drug loading in the nanoparticles" refers the ratio of the drug that has been encapsulated into the excipient to the total content of its dose. It can be determined according to known methods, for example by filtration followed by determination of the residual content of drug in the supernatant. The lesser is the content of the drug in the supernatant, the more efficient is the drug loading.

The term "stabilizing agents" is used to indicate excipients that act as surface stabilizer, and growth modifier, during the nanoparticles preparation.

The term "wetting agents" is used to indicate excipients that helps the dispersion of the nanoparticles in the aqueous vehicle and the homogeneity of the suspension.

The term "extemporaneous preparation" is used to designate all those cases in which the pharmaceutical formulation is not manufactured ready-to-use, rather to be prepared at a time subsequent to that in which the powder is manufactured, usually a time close to the time of administration to the patient.

For a formulation in form of extemporaneous preparation, the expression "chemically stable" refers to a formulation that, upon storage at room temperature (25° C.±2° C.) for at least three days and/or under refrigerated conditions (2-8° C.) for at least one week, shows no significant drug degradation.

For a formulation in form of extemporaneous preparation, the expression "physically stable" refers to a formulation that, at room temperature (25° C.±2° C.) and/or under refrigerated conditions (2-8° C.), exhibits no significant growth in particle size during storage for at least three days and/or for at least one week, respectively. During said periods, it turns out to be readily redispersible, and upon redispersion, neither agglomerates nor quick separation from the aqueous vehicle are observed.

The term "therapeutically effective amount" means the amount of the active ingredient in the formulation, that, when delivered to the patients, provides the desired biological effect.

The term "treatment" refers to the therapeutic use for palliative, curing, symptom-allievating, symptom-reducing, disease regression-inducing therapy.

DETAILED DISCLOSURE OF THE INVENTION

The aim of the present invention is to provide a safe, aqueous pharmaceutical formulation for intraduodenal administration comprising carbidopa and melevodopa as active ingredients in a ratio of 1:5 by weight, and one or more excipients, wherein melevodopa is completely dissolved, and carbidopa is present as nanoparticles having a volume diameter comprised between 100 and 1000 nm, preferably from 200 to 900 nm.

Advantageously, the vehicle is made of water, preferably of water for injection.

The use of carbidopa with a particle size in the nanometer range should not be confused with the particle size in the micron range reported in the prior art.

Carbidopa could be used as anhydrous form or as monohydrate.

Advantageously, the concentration of melevodopa is comprised between 50 and 150 mg/ml, preferably between 100 and 125 mg/ml expressed as levodopa, and the concentration of carbidopa is comprised between 5 and 30 mg/ml, expressed as anhydrous carbidopa, preferably between 10 and 30 mg/ml, more preferably between 10 and 20 mg/ml, even more preferably between 15 and 20 mg/ml.

The excipients should be pharmaceutically acceptable for the duodenal administering system.

Advantageously, the excipients comprise a stabilization agent and/or a wetting agent.

The stabilization agent may be selected from the group consisting of hydroxypropyl methylcellulose (HPMC), polyvinylpyrrolidone (PVP), vinylpyrrolidone-vinyl acetate copolymers, methacrylic copolymers, carboxymethylcellulose, carbomers, plant gums and colloids such as xantan gum, guar gum, pectin, agar, alginates, dextran and other polysaccharides and derivatives thereof.

The wetting agent may be selected from the group consisting of pharmaceutically acceptable salts of fatty acids such as sodium octanoate, poloxamers, polysorbates, and sorbitan mono laurate.

In a particular embodiment, the carbidopa nanoparticles could be prepared by a process comprising the steps of: i) dissolving carbidopa in the presence of one or more excipients in an acidic aqueous solution of HCl; ii) generating the carbidopa nanoparticles by controlled precipitation against a basic aqueous solution as anti-solvent using micro jet reactor technology; and iii) removing the aqueous medium.

Details and operative parameters of the micro jet reactor technology are disclosed in US 2011/0294770 whose teaching is incorporated herein by reference.

In order to optimize the precipitation step, the person skilled in the art shall properly adjusted all the parameters according to its knowledge, in particular the flow rates of the aqueous solution and their mixing ratio.

Advantageously, the ratio between the solvent phase i) and the anti-solvent phase ii) is comprised between 1:1 and 1:10 v/v.

Preferably, the pH of the acidic aqueous solution of step i) is comprised between 1.0 and 2.0, more preferably between 1.1 and 1.5, while HCl is used at a concentration of 0.4-0.8 N, more preferably of 0.6 N.

The excipient may be added to the aqueous phase i) and/or to the anti-solvent phase ii).

Preferably the excipient is selected from the group consisting of vinylpyrrolidone-vinyl acetate copolymers, methacrylic copolymers, and polysorbates alone or as a mixture thereof.

Vinylpyrrolidone-vinyl acetate copolymers are currently available on the market as Kollidon™ from BASF GmbH (Ludwigshafen, Germany), while methacrylic copolymers are on the market as Eudragit™ and could be purchased from Evonik Rohm GmbH (Darmstadt, Germany).

Polysorbates are commercially available as Tween 20 and Tween 80 from Sigma-Aldrich Chemie (Buchs, Germany).

More preferably, the excipient is a mixture of Eudragit L100, Kollidon VA64 and Tween 20, even more preferably in a mixture of 20:5:5 parts w/w/w.

Preferably, the pH of the basic aqueous solution of step ii), used as anti-solvent, is comprised between 12.0 and 14.0, more preferably between 13 and 13.8, while NaOH is used at a concentration of 0.4-0.8 M, more preferably of 0.5-0.7 M, even more preferably of 0.6 M.

In fact, it has been found that by proper selection of the solvent and anti-solvent phases i) and ii) as well as of the excipients, it would be possible to achieve a high drug loading, advantageously equal to or higher than 65% by weight, preferably higher than 70%, more preferably equal to or higher than 80%, and even more preferably equal to or higher than 90%.

With such a high drug loading, agglomeration and/or particle growth may be avoided upon resuspension of the nanoparticles in an aqueous vehicle.

A low drug loading may also cause homogeneity problems.

Furthermore, due to the high drug loading, the stability of the powdery pharmaceutical preparation during its handling and storage is improved without the need of keeping the nanoparticles in strictly controlled conditions of temperature and/or relative humidity.

Elimination of the aqueous medium in step iii) could be performed according to procedures reported in the art.

The obtained nanoparticles could also be dried according to procedures reported in the art.

Typically, said process provides nanoparticles with a particle size of 400-900 nanometers.

In an alternative embodiment, the carbidopa nanoparticles could be prepared by controlled reduction of the drug substance particle size through a wet bead milling process to a sub-micron size.

Briefly, the particles are obtained by passing a suspension of the active ingredient, through a wet bead mill until its particle size has been reduced to sub-micron or 'nano' size to form a colloid.

Therefore, said process comprises the steps of: i) suspending carbidopa in the presence of one or more excipients in an acidic aqueous solution; ii) milling the obtained suspension; and iii) removing the aqueous medium.

Advantageously the pH is adjusted with an organic acid, preferably citric acid at a value of 4.5 to 5.5, preferably from 5.0 to 5.2.

Preferably, oxygen is preliminary eliminated from the aqueous solution i).

Advantageously, carbidopa is suspended in the aqueous medium i) at a concentration comprised between 5 and 20 mg/ml, preferably of 10 mg/ml.

Preferably, the excipient added to said acidic aqueous phase i) is a stabilizing agent selected from the group of hydroxypropyl methylcellulose (HPMC), and polyvinylpyrrolidone (PVP), optionally in combination with a wetting agent selected from the group of sodium octanoate and poloxamers.

Said excipients are commercially available, for example from Sigma-Aldrich Chemie (Buchs, Germany).

More preferably, the excipient is a mixture of HPMC, PVP K30 and poloxamer 188 or sodium octanoate, even more preferably in a ratio of about 45:45:10% w/w/w.

In fact, it has been found that by a proper selection of the solvent phase i) as well as of the excipients, it is possible to achieve chemical stability of carbidopa and good physical stability and homogeneity of the formulation once resuspended in the aqueous vehicle.

The skilled person in the art shall properly adjust the conditions of milling depending on the particle size to be achieved.

Typically, milling is performed at a rotation speed of 400 to 600 r.p.m. for a time of 8-12 hours.

Typically, said process provides nanoparticles with a particle size of 200-600 nanometers.

Elimination of the solvent in step iii) could be performed according to procedures reported in the art. The obtained nanoparticles could also be dried according to procedures reported in the art.

Whatever process is used, the carbidopa nanoparticles are then mixed with melevodopa in the suitable ratio.

The invention is also directed to a process for preparing the formulation of the invention comprising the steps of: i) adding the carbidopa nanoparticles to an aqueous solution comprising melevodopa in a ratio of 1:5 by weight, and one or more excipients.

In an alternative embodiment, the formulation of the invention is in form of a powder to be reconstituted before use.

Therefore, the present invention is also directed to a process for preparing the formulation comprising the steps of: i) adding the carbidopa nanoparticles to an aqueous solution comprising melevodopa and one or more cryoprotectant agents as excipients; and ii) removing the residual water by drying.

Advantageously, the drying step ii) could be performed according to methods and conditions known to the skilled person in the art.

For example, the drying step could be performed by spray-drying or freeze-drying, preferably by freeze-drying.

Advantageously, the cryoprotectant agent is selected from the group consisting of mannitol, glycerol, propylene glycol, glycine, sucrose, lactose and trehalose, and mixtures thereof in any ratio by weight.

The formulation of the invention may comprise other additional excipients, which are well-known to those skilled in the art. As examples of such excipients may be mentioned antioxidants, preserving agents and pH regulating agents. Such excipients may be added to the formulation before, during or after the dispersion process.

After drying, the pharmaceutical formulation is harvested to obtain a powder to be stored and reconstituted before use or re-suspended in a proper aqueous vehicle to provide an extemporaneous pharmaceutical formulation.

Advantageously the pH of the aqueous pharmaceutical formulation is comprised between 4.0 and 6.0, preferably between 4.5 and 5.5.

Advantageously, the aqueous formulation of the invention has a viscosity of at least 50 mPas, preferably of 100 to 250 mPas, measured at a moderate shear rate, according to procedures known to the skilled person in the art.

In case, the concentration and the type of the excipient shall be properly adjusted to achieve the desired viscosity as is well-known to those skilled in the art.

In an alternative embodiment, the extemporaneous formulation is prepared by dispersing the powder in the aqueous vehicle using methods and apparatus, which are well-known to those skilled in the art.

In a preferred embodiment of the invention, the aqueous pharmaceutical formulation is filled and stored under exclusion of oxygen.

For a period sufficient for its use by the patient, said formulation turned out to be physically and chemically stable, while maintaining good homogeneity.

In particular, under refrigerated conditions, the formulation of the invention turned out to be physically and chemically stable for at least six weeks.

In a preferred embodiment of the invention, when carbidopa nanoparticles are prepared by micro jet reactor technology, the formulation comprises the following excipients: Eudragit L100, Kollidon VA64 Tween 20, mannitol and trehalose.

In another preferred embodiment, when carbidopa nanoparticles are prepared by wet bead milling, the formulation comprises the following excipients: melevodopa, carbidopa HPMC, PVP K30, poloxamer 188 or sodium octanoate, mannitol and trehalose.

The formulation of the invention may comprise further active ingredients, i.e. COMT inhibitors such as opicapone, entacapone and tolcapone, safinamide, memantine, selegiline, preferably a COMT inhibitor.

Once dispersed in water, the formulation of the invention could be filled into suitable containers for intraduodenal administration. Such containers may have a volume of up to 100 ml, preferably up to 50 ml, more preferably of 20 ml.

In fact, due to the higher concentrations of two active ingredients, the aqueous formulations of the invention require lower volumes that the formulations of the prior art. Furthermore, its viscosity does not need to be as higher as the formulations of the art.

Therefore, the claimed formulation could be dispensed with lesser bulky infusion pumps such as the Synchromed II model 8637-40 (Meditronic, Modena, Italy) or the Crono pump (Canè SpA, Torino, Italy).

The dose to be administered during a given period of time is determined by the physician on the basis of such criteria as the age and weight of the patient and the severity of the condition.

As has been stated above, it is an important feature of the invention that the formulations are prepared and stored under exclusion of oxygen. Thus, the formulation may be dispensed into bag-like containers of a plastic sheet material having a low permeability for oxygen. Furthermore, the filling of these containers may be carried out in such a manner that all air is first sucked out of the containers, after which the desired amount of the formulation is pumped into the containers, and the containers are subsequently sealed. The containers are also provided with an outlet conduit, which is initially sealed, and is only opened immediately before the conduit is connected to a catheter for intraduodenal administration. By this arrangement, the container may also be emptied completely without any need for an air valve in the container.

The container with the formulation of the invention is usually placed in a type of cassette adapted to be carried by the patient. Such cassettes are previously known, and are provided with the infusion pump for administering a metered amount of the formulation over a given time.

The formulation of the invention could be utilized for the treatment of any form of Parkinson's disease, in particular for the treatment of patients affected by advanced Parkinson disease with serious, unpredictable and rapid changing motor fluctuations and dyskinesia.

The invention is illustrated with reference to the following examples.

EXAMPLES

Example 1

Preparation of Carbidopa Nanoparticles by Microjet Reactor Technology Under Different Conditions In order to prepare the nanoparticles, carbidopa was dissolved in different solvent systems in a concentration of 50 to 200 mg/mL in the presence of different excipients.

These solutions were subjected to precipitation against different anti-solvent phases using the microjet reactor technology.

Some representative results are reported in Table 1.

TABLE 1

| Sample | Carbidopa [mg/mL] | Solvent phase | Excipient [mg/mL] | Non-solvent phase | Evaluation |
|---|---|---|---|---|---|
| 1 | 49 | Acetone:3N HCl 9:1 v/v | Eudragit L100 9.8 mg/ml | 1M NaoH | No precipitation |
| 2 | 49 | Acetone:3N HCl 9:1 v/v | Eudragit L100 9.8 mg/ml | Water | No precipitation |

TABLE 1-continued

| Sample | Carbidopa [mg/mL] | Solvent phase | Excipient [mg/mL] | Non-solvent phase | Evaluation |
|---|---|---|---|---|---|
| 3 | 176 | 0.6N HCl | Eudragit L100 10 mg/ml | 0.6M NaOH | precipitation |
| 4 | 80 | Water:formic acid 1:1.5 v/v | Kollidon VA64 10 mg/ml | 0.7M NaOH | degradation |

As it can be appreciated, chemically stable carbidopa nanoparticles precipitate from 0.6 N HCl aqueous solution, while in other conditions precipitation does not occur or degradation is observed.

Example 2

Preparation of Melatonin Nanoparticles by Microjet Reactor Technology and Evaluation of the Drug Loading In order to prepare the nanoparticles, carbidopa was dissolved in 0.6 N HCl aqueous solution in a concentration of about 176 mg/mL in the presence of different excipients.

These solutions were precipitated against NaOH at different concentrations using the microjet reactor technology. During the precipitation process, flow rate of carbidopa solution was adjusted to 1-4 ml/min and the flow rate of the anti-solvent was adjusted to 10 mL/min.

A gas pressure of 0.1 or 0.2 bar was used to ensure the production of homogenous nanoparticles.

The microjet reactor temperature was adjusted to 25-40° C. throughout the precipitation process.

Residual water was removed by drying.

In order to determine the drug loading, the free carbidopa concentration in the aqueous phase, nanoparticles were filtered through 0.02 μm syringe filters and centrifuge at 16000 r.p.m. for 90 min.

Carbidopa nanoparticles were also characterized in terms of particle size by measuring their diameter through Dynamic Light scattering (DLS).

The results are reported in Table 2.

All the samples have a particle size comprise between 600 and 900 nanometers.

As it can be appreciated, by proper selection of the condition, carbidopa nanoparticles with drug loading ranging from 70 to 90% could be prepared.

Example 3

Preparation of Melatonin Nanoparticles by Wet Bead Milling

Carbidopa nanoparticles were produced by wet bead milling.

Briefly, carbidopa (10 mg/mL drug load) was suspended in a degassed citric acid pH 5.01 aqueous solution (0.6 ppm $O_2$ levels), different excipients were added and the suspension milled at 530 rpm for 12 h.

Residual water was removed by drying.

The carbidopa nanoparticles were dried and mixed with melevodopa.

The powders were dispersed in an aqueous vehicle to obtain two formulations having the following compositions:

Formulation 1: 10 mg/mL carbidopa, 50 mg/mL melevodopa, 0.1% w/v sodium metabisulfite, 0.5% HPMC 606, 0.5% PVP K30, 0.1% sodium octanoate Formulation 2: 10 mg/mL carbidopa, 50 mg/mL melevodopa, 0.1% w/v sodium metabisulfite, 0.5% HPMC 606, 0.5% PVP K30, 0.1% poloxamer 188

The samples were placed on stability storage in sealed vials at 2° C.-8° C. and 25° C./60% RH and analysed at t=0, 1, 3, 7 and 14 days. A qualitative monitoring of the dispersion state of the nano-emulsion, i.e., zeta size potential, polydispersity index (PdI), change of particle size with time and particle migration was assessed by light scattering techniques (dynamic light scattering and multiple light scattering).

TABLE 2

| Sample | Carbidopa [mg/mL] | Solvent | Anti-solvent | Kollidon VA64 [mg/mL] | Conc Eudragit L100 [mg/mL] | Tween 20 [mg/mL] | Tween 80 [mg/mL] | Drug loading [%] |
|---|---|---|---|---|---|---|---|---|
| 1 | 176.47 | 0.6N HCl | 0.7M NaOH | 5 | 20 | | | 86.61 |
| 2 | 176.47 | 0.6N HCl | 0.6M NaOH | 5 | 20 | | | 83.02 |
| 3 | 176.47 | 0.6N HCl | 0.5M NaOH | 5 | 20 | | | 70.10 |
| 4 | 176.47 | 0.6N HCl | 0.4M NaOH | 5 | 20 | | | 55.91 |
| 5 | 176.47 | 0.6N HCl | 0.7M NaOH | 5 | 20 | 5 | | 86.63 |
| 6 | 176.47 | 0.6N HCl | 0.6M NaOH | 5 | 20 | 5 | | 87.34 |
| 7 | 176.47 | 0.6N HCl | 0.5M NaOH | 5 | 20 | 5 | | 73.26 |
| 8 | 176.47 | 0.6N HCl | 0.4M NaOH | 5 | 20 | 5 | | 53.39 |
| 9 | 176.47 | 0.6N HCl | 0.7M NaOH | 5 | 20 | | 5 | 85.55 |
| 10 | 176.47 | 0.6N HCl | 0.6M NaOH | 5 | 20 | | 5 | 90.00 |
| 11 | 176.47 | 0.6N HCl | 0.5M NaOH | 5 | 20 | | 5 | 74.39 |
| 12 | 176.47 | 0.6N HCl | 0.4M NaOH | 5 | 20 | | 5 | 54.12 |
| 13 | 176.47 | 0.6N HCl | 0.7M NaOH | 5 | 20 | | | 86.03 |
| 14 | 176.47 | 0.6N HCl | 0.6M NaOH | 5 | 20 | | | 87.75 |
| 15 | 176.47 | 0.6N HCl | 0.4M NaOH | 5 | 20 | | | 54.48 |

X-ray powder diffraction (XRPD) was employed to investigate physical form integrity.

For particle size measurement and polydispersity index determination by DLS, 100 μL of each prepared formulation was diluted in 1 ml of type I water (previously filtered) and the derived count rate was monitored by using photon correlation spectroscopy (Malvern Nanoseries Zetasizer, Malvern Instruments Ltd., Malvern, UK). Measurements were taken at 25° C. at a scattering angle of 173°. Refractive index and viscosity constants were set at 1.458 and 60 mPa·s, respectively.

Multiple scattering was conducted by placing the formulations into cylindrical glass tubes and submitted to Turbiscan Lab® classic analysis. The analysis of the formulations was carried out as a variation of back-scattering profiles (BS). The obtained BS data were then elaborated as BS profiles by the Turbiscan Converter. Measurements were carried out using a pulsed near infrared LED at a wavelength of 850 nm for 1 h. Two different synchronous optical sensors received the light transmitted through and backscattered by samples at an angle of 180° and 45° with respect to the incident radiation, respectively. The two sensors scanned the entire height (~8 mm) of the prepared formulations.

The results are reported in Table 3.

The results are reported in Table 4.

TABLE 4

| Time point (days) | F1 2° C.-8° C. | F2 25° C. (60% RH) | F2 2° C.-8° C. | F2 25° C. (60% RH) |
|---|---|---|---|---|
| Average % of carbidopa ||||| 
| 1 | 94.87 | 92.0 | 95.02 | 96.37 |
| 7 | 95.68 | 94.49 | 93.21 | 94.07 |
| 17 | 95.39 | 94.29* | 94.93 | 92.31* |
| Average % of melevodopa ||||| 
| 1 | 89.95 | 87.82 | 92.92 | 92.82 |
| 7 | 88.80 | 82.49 | 90.92 | 86.44 |
| 17 | 83.99 | 71.43* | 86.11 | 71.96* |
| Average % of L-dopa impurity ||||| 
| 1 | 3.39 | 4.55 | 3.20 | 4.33 |
| 7 | 4.41 | 8.42 | 4.38 | 7.60 |
| 17 | 9.57 | 24.84 | 8.35 | 22.77 |

*Colour change

Both formulations exhibits good chemical stability for at least 3 days upon storage at room temperature and/or under refrigerated conditions.

TABLE 3

| | | Size (nm) Time (days) | | | | Polydispersity index Time (days) | | | |
|---|---|---|---|---|---|---|---|---|---|
| Formulation | T °C. | 1 | 3 | 7 | 14 | 1 | 3 | 7 | 14 |
| F1 | 2-8 | 268 ± 57.1 | 352 ± 107 | 416 ± 148.2 | 413 ± 182 | 0.62 ± 0.02 | 0.64 ± 0.09 | 0.79 ± 0.13 | 0.68 ± 0.09 |
| | 25 | 343 ± 95.2 | 463 ± 75.4 | 548 ± 117 | 392 ± 69 | 0.7 ± 0.07 | 0.8 ± 0.1 | 0.79 ± 0.1 | 0.79 ± 0.09 |
| F2 | 2-8 | 227 ± 66.1 | 431 ± 133 | 338 ± 53.7 | 403 ± 27 | 0.5 ± 0.16 | 0.77 ± 0.05* | 0.68 ± 0.09 | 0.86 ± 0.06 |
| | 25 | 233 ± 43.4 | 332 ± 41.9* | 405 ± 146 | 335 ± 9.7 | 0.5 ± 0.03 | 0.71 ± 0.07** | 0.7 ± 0.18 | 0.7 ± 0.1 |

*p < 0.05;
**p < 0.01 for all tested samples at each described condition. One-way analysis of variance.

As it can be appreciated, the particle size did not statistically change (p<0.05) for at least seven days for both formulations when stored at room temperature and/or under refrigerated conditions.

The PdI values of the samples indicate a highly polydispersed system in terms of particle distribution. However, these values were stable for F1 under both storage conditions, whereas, a little increase was observed for F2 (p<0.05) at 3 days.

On the other hand, when subjected to sedimentation analysis by Turbiscan, and both formulations exhibit good homogeneity and a low tendency to sedimentation for at least 3 days, when stored at room temperature.

The PXRD patterns observed for both samples show similar trend to that of the carbidopa which is indicative of the presence of the same parent material exhibiting its unique structure.

The formulations F1 and F2 were also assayed for carbidopa and melevodopa content by HPLC-UV at 1, 7 and 17 days.

A first colour change was observed in the solutions stored at 25° C. at t=170 days and no change in colour was noticed for the ones under refrigerated conditions. The amount of L-dopa impurity started to increase at room temperature over 5% after 4 days.

Example 4

Lyophilized Formulation

Carbidopa nanoparticles having the composition according to sample 10 of Table 2 of Example 2 are prepared. Said nanoparticles are added to an aqueous solution comprising melevodopa and mannitol as cryoprotectant agent, then lyophilized.

The obtained powder formulation is dispersed in an aqueous solution to achieve a concentration of 125 mg/ml melevodopa and 25 mg/ml carbidopa.

The invention claimed is:

1. An aqueous pharmaceutical formulation for intraduodenal administration, comprising carbidopa and melevodopa as active ingredients in a ratio of 1:5 by weight, and one or more excipients, wherein said melevodopa is completely dissolved, and said carbidopa is present as nanoparticles having a volume diameter of 100 to 1000 nm.

2. The formulation according to claim 1, wherein said nanoparticles have a volume diameter of 200 to 900 nm.

3. The formulation according to claim 1, wherein said one or more excipients comprise a component selected from the group consisting of a stabilization agent, a wetting agent, and mixtures thereof.

4. The formulation according to claim 3, wherein said stabilization agent is selected from the group consisting of hydroxypropyl methylcellulose, polyvinylpyrrolidone, a vinylpyrrolidone-vinyl acetate copolymer, a methacrylic copolymer, carboxymethylcellulose, a carbomer, a plant gum, and a plant colloid, and mixtures thereof.

5. The formulation according to claim 3, wherein said wetting agent is selected from the group consisting of a pharmaceutically acceptable salt of a fatty acid, a poloxamer, a polysorbate, sorbitan monolaurate, and mixtures thereof.

6. The formulation according to claim 1, which further comprises one or more additional excipients selected from the group consisting of an antioxidant, a preserving agent, a pH regulating agent, and mixtures thereof.

7. The formulation according to claim 1, wherein said carbidopa nanoparticles are prepared by a process comprising:
   i) suspending carbidopa in the presence of one or more excipients in an acidic aqueous solution;
   ii) milling the obtained suspension; and
   iii) removing the aqueous medium.

8. The formulation according to claim 1, wherein said carbidopa nanoparticles are prepared by a process comprising:
   i) dissolving carbidopa in the presence of one or more excipients in an acidic aqueous solution of HCl;
   ii) generating the carbidopa nanoparticles by controlled precipitation against a basic aqueous solution as antisolvent using micro jet reactor technology; and
   iii) removing the aqueous medium.

9. The pharmaceutical formulation according to claim 8, wherein at least one of said excipients is adsorbed on the surface of the carbidopa nanoparticles in such a way as that said carbidopa nanoparticles are coated by the excipient.

10. A pharmaceutical formulation according to claim 1, which is in a form of a dried powder to be reconstituted in water before use.

11. A pharmaceutical formulation according to claim 1, wherein, said melevodopa is present in a concentration of 50 to 150 mg/ml, expressed as levodopa, and said carbidopa is present in a concentration of 5 to 30 mg/ml, expressed as carbidopa anhydrous.

12. The pharmaceutical formulation according to claim 11, wherein said melevodopa is present in a concentration of 100 to 125 mg/ml, and said carbidopa is present in a concentration of 15 to 20 mg/ml.

13. A method for the treatment of Parkinson's disease, comprising administering to a subject in need thereof an effective amount of a formulation according to claim 1.

14. A kit, comprising: a) a pharmaceutical formulation according to claim 10; b) a pharmaceutically acceptable aqueous vehicle; c) container means for containing the pharmaceutical formulation, and the aqueous vehicle; and d) an infusion pump.

15. The formulation according to claim 3, wherein said stabilization agent is selected from the group consisting of xantan gum, guar gum, pectin, agar, an alginate, dextran, and mixtures thereof.

16. The formulation according to claim 3, wherein said wetting agent comprises sodium octanoate.

* * * * *